US00PP07780P

United States Patent [19]

Holtkamp, Sr.

[11] Patent Number: Plant 7,780

[45] Date of Patent: Feb. 4, 1992

[54] AFRICAN VIOLET PLANT NAMED EMILIE

[76] Inventor: Reinhold Holtkamp, Sr., Blumenstrasse 28, D 4242 Rees-Haffen, Fed. Rep. of Germany

[21] Appl. No.: 565,322

[22] Filed: Aug. 10, 1990

[51] Int. Cl.[5] ..... A01H 5/00

[52] U.S. Cl. ..... Plt./69

[58] Field of Search ..... Plt./69

[56] References Cited

U.S. PATENT DOCUMENTS

P.P. 5,063 6/1983 Fischer ..... Plt. 69

*Primary Examiner*—James R. Feyrer

*Attorney, Agent, or Firm*—Foley & Lardner

[57] ABSTRACT

A new and distinct cultivar of African violet named Emilie characterized by its blue, star-shaped flowers; strong, upright flower stems that curve slightly toward the center to form a bouquet above the leaves; dark green, spear-shaped leaves; profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Emilie.

The new cultivar was referred to during the breeding and selection process by the designation 31 stahl.bl. and is a product of a planned breeding program. The new cultivar was originated from a cross made by me in the controlled breeding program in Haffen, Federal Republic of Germany. The female, or seed parent was a cultivar designated D 14. The male, or pollen parent was a cultivar designated E 33.

Emilie was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Emilie has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commerical practice.

The following traits have been repeatedly observed and are determined to be basic characteristics of Emilie, which in combination distinguish this African violet as a new and distinct cultivar:

(1) Strong, upright flower stems curving slightly toward the center.

(2) Blue, star-shaped flowers.

(3) Profuse flowering.

(4) Each plant carries 8–10 and more upright flower stems each of which carries 7–12 and more flowers.

(5) Long lasting, non-dropping flowers.

(6) Vigorous grower.

(7) Plant saleable 10 toll weeks after potting.

(8) Seed capsules push slightly through.

(9) Dark green, spear-shaped leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Emilie.

Parentage:

*Male parent.*—E 33.

*Female parent.*—D 14.

Propagation: The new cultivar holds its distinguishing characteristics through successive propagations by leaf cuttings.

Plant: From 9 cm to 11 cm tall when grown in pots, and approximately 24–28 cm in diameter when fully grown.

Leaves:

*General form.*—Spear-shaped.

*Diameter.*—60–65 mm wide and 70–85 mm long.

Texture.—Leatherlike.

*Aspect.*—Hairy, slightly shiny, slightly serrated.

*Veins.*—Upperside: visible; underside: well pronounced, light green or purplish green, shiny.

*Color (upperside).*—Yellow-Green Group 147 A and darker.

*Color* (underside).—Greyed-Purple Group 186 A.

*Petiole.*—Strong, upright, purplish brown, hairy.

Flowers:

*Buds.*—Bell-shaped, 7–9 mm just before opening, light green with purplish touch.

*Sepals.*—Five (5). Color: Purplish brown.

*Calyx.*—Shape: Funnel-shaped. Aspect: Spear-shaped, hairy.

*Peduncle.*—Character: Strong upright, hairy. Color: Purplish brown.

Individual flowers:

*Size.*—45-50 mm.

*Shape.*—Star-shaped.

*Color (upperside).*—Violet-Blue Group 93 B to C. Under cooler temperatures and more intensive lighting, the blue color tends to intensify.

*Color (underside).*—Violet Group 88 C to D.

*Borne.*—Each flower stem carries 7-12 and more flowers on strong, upright peduncles that are free standing above the leaves, thereby forming a compact bouquet.

Flowering habit: Flowers 10-11 weeks after potting.

Reproductive organs:

*Stamens.*—Five (5). Anthers: 5 composed of 10 anther cells, seed capsule pushes slightly through.

*Filaments.*—Yellowish green with purplish blue on edges, 4-5 mm long.

*Pollen color.*—Yellow Group 7 A.

*Styles.*—7-8 mm long, purplish blue, base of ovary light green and hairy.

Roots: Normally developed, white when young, turning slightly brownish when older.

Disease resistance: Up to date, Emilie has shown very good resistance to all major violet diseases.

General observations: Emilie is an attractive, vigorous grower with blue flowers contrasting nicely with the bright yellow anthers and dark green, spear-shaped, leaves. A bouquet of flowers free standing above the leaves develops after approximately 10-11 weeks. Each of the 8-12 and more strong flower stems carries 7-12 and more star-shaped flowers. The flowers are long-lasting and non-dropping and the seed capsules push slightly through.

I claim:

1. A new and distinct cultivar of African violet named Emilie, as described and illustrated, and particularly characterized by its blue, star-shaped flowers; strong, upright flower stems that curve slightly toward the center to form a bouquet above the leaves; dark green, spear-shaped leaves; profuse flowering, vigorous growth habit, flowering 10-11 weeks after potting, and its long lasting and non-dropping flowers.

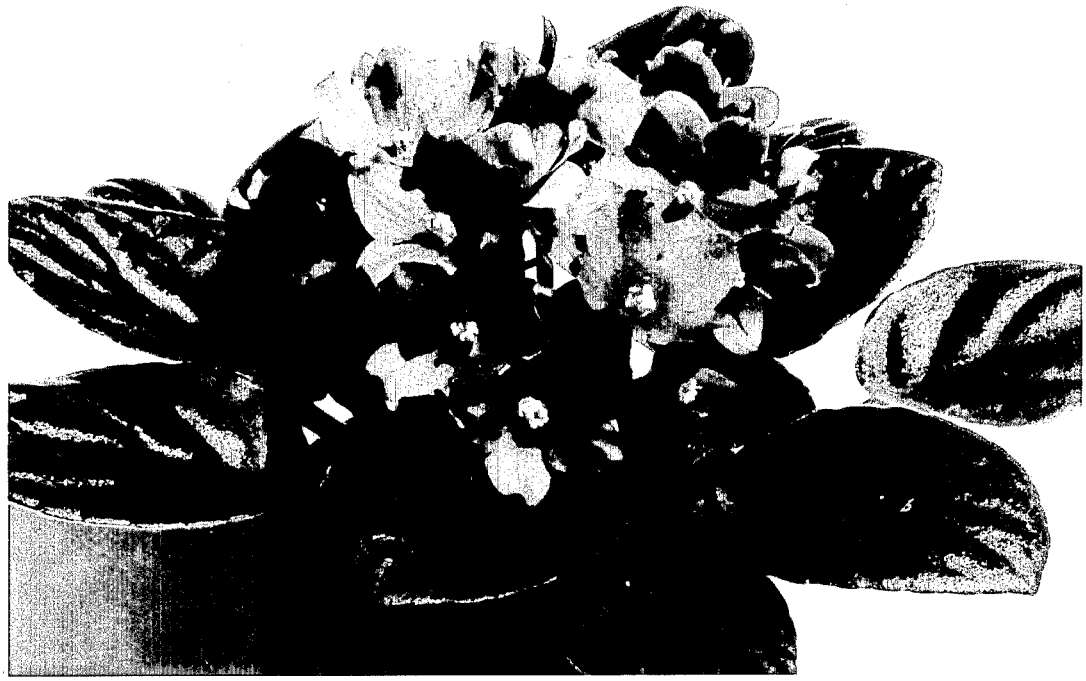

* * * * *